United States Patent
McMillan et al.

(10) Patent No.: US 9,260,715 B2
(45) Date of Patent: *Feb. 16, 2016

(54) METHOD OF INDUCING AN IMMUNE RESPONSE

(75) Inventors: Nigel McMillan, Brisbane (AU);
Graham Leggatt, Brisbane (AU);
Wenyi Gu, Brisbane (AU)

(73) Assignee: The University of Queensland, St. Lucia, Queensland (AU)

( * ) Notice: Subject to any disclaimer, the term of this patent is extended or adjusted under 35 U.S.C. 154(b) by 0 days.

This patent is subject to a terminal disclaimer.

(21) Appl. No.: 13/530,002

(22) Filed: Jun. 21, 2012

(65) Prior Publication Data

US 2012/0269850 A1  Oct. 25, 2012

Related U.S. Application Data

(62) Division of application No. 11/900,412, filed on Sep. 11, 2007, now Pat. No. 8,227,436.

(60) Provisional application No. 60/880,547, filed on Jan. 16, 2007.

(51) Int. Cl.
| *A61P 37/02* | (2006.01) |
| *C12N 15/11* | (2006.01) |
| *C12N 15/113* | (2010.01) |

(52) U.S. Cl.
CPC .......... *C12N 15/111* (2013.01); *C12N 15/1131* (2013.01); *C12N 2310/14* (2013.01); *C12N 2320/30* (2013.01)

(58) Field of Classification Search
USPC ............. 435/6, 91.1, 91.31, 455, 5, 6.1, 6.14, 435/7.1, 458; 514/1, 2, 44; 536/23.1, 24.5, 536/24.32; 424/184.1, 204.1, 277.1
See application file for complete search history.

(56) References Cited

U.S. PATENT DOCUMENTS

| 7,427,605 | B2 | 9/2008 | Davis et al. | |
| 7,718,629 | B2 | 5/2010 | Bumcrot et al. | |
| 8,227,436 | B2 * | 7/2012 | McMillan et al. | 514/44 A |
| 2003/0143732 | A1 | 7/2003 | Fosnaugh et al. | |
| 2003/0170891 | A1 | 9/2003 | McSwiggen | |
| 2004/0259247 | A1 | 12/2004 | Tuschl et al. | |
| 2006/0263435 | A1 | 11/2006 | Davis et al. | |
| 2007/0004664 | A1 | 1/2007 | McSwiggen et al. | |
| 2007/0031844 | A1 | 2/2007 | Khvorova et al. | |
| 2007/0281899 | A1 | 12/2007 | Bumcrot et al. | |
| 2009/0149403 | A1 | 6/2009 | MacLachlan | |
| 2011/0015250 | A1 | 1/2011 | Bumcrot et al. | |
| 2011/0269816 | A1 * | 11/2011 | Kaspar et al. | 514/44 A |
| 2012/0244207 | A1 | 9/2012 | Fitzgerald et al. | |

FOREIGN PATENT DOCUMENTS

| WO | WO 93/23569 | * 11/1993 |
| WO | WO 2004/080406 | 9/2004 |
| WO | WO 2004/090108 | 10/2004 |
| WO | WO 2010/147992 | 12/2010 |

OTHER PUBLICATIONS

Kuck, D. et al., Vaccine, vol. 24, pp. 2952-2965 (2006).*
Alvarez-Obregon, J.C. et al., Vaccine, vol. 19, pp. 47-64 (2004).*
Peracchi, A. et al., Rev. Med. Virol., vol. 14, pp. 47-64 (2004).*
Chirila, T. et al., Biomaterials, vol. 23, pp. 321-342 (2002).*
Agrawal, S. et al., Molecular Med. Today, vol. 6, pp. 72-81 (2000).*
Crooke, S., Annu. Rev. Med., vol. 55, pp. 61-95 (2004).*
Branch, A., Trends in Biochem. Sci., vol. 23, pp. 45-50 (1998).*
Yu et al., Proc. Nat'l. Acad. Sci., vol. 99, No. 9, pp. 6047-6052 (2002).*
Agrawal, S., et al., "Antisense oligonucleotides: towards clinical trials." Trends in Biotechnology. Oct. 1996, vol. 14, pp. 376-387.
Australian Government—IP Australia, Patent Examination Report No. 1, Australian Patent Application No. 2007344641, Aug. 14, 2012, 4 Pages.
Bass, B., "The short answer," Nature, May 24, 2001, pp. 428-429, vol. 411.
Elbashir, S., et al., "Analysis of gene function in somatic mammalian cells using small interfering RNAs," Methods, 2002, pp. 199-213, vol. 26.
Elbashir, S., et al., "Duplexes of 21-nucleotide RNAs mediate RNA interference in mammalian cell culture," Nature, May 24, 2001, p. 494-498, vol. 411.
Elbashir, S., et al., "Functional Anatomy of siRNAs for Mediating Efficient RNAi in *Drosophila melanogaster* Embryo Lysate", The EMBO Journal, 2001, pp. 6877-6888, vol. 20, No. 23.
Elbashir, S., et al., "RNA Interference is Mediated by 21-and 22 Nucleotide RNAs," Genes & Development, 2001, pp. 188-200, vol. 15.
Fire, A., "RNA-triggered Gene Silencing," Trends in Genetics, Sep. 1999, pp. 358-363, vol. 15, No. 9.
Fire, A., et al., "Potent and Specific Genetic Interference by Double Stranded RNA in Caenorhabditis elegans," Nature, Feb. 19, 1998, pp. 806-811, vol. 391.

(Continued)

*Primary Examiner* — Jane Zara
(74) *Attorney, Agent, or Firm* — Fenwick & West LLP

(57) ABSTRACT

A method is provided for inducing or enhancing an immune response in a mammal to a target polypeptide expressed in a plurality of cells of the mammal, which method comprises administering to the mammal an inhibitory nucleic acid which targets a region of a ribonucleic acid (RNA) which encodes said polypeptide. Also provided is a pharmaceutical composition comprising an inhibitory nucleic acid which targets a region of an RNA which encodes a target polypeptide expressed in a plurality of cells of a mammal, such that translation of an aberrant form of the target polypeptide occurs in said cells, said truncated form of the target polypeptide comprising one or more T cell epitopes; together with a pharmaceutically acceptable carrier or diluent.

14 Claims, 3 Drawing Sheets

(56) References Cited

OTHER PUBLICATIONS

Patent Cooperation Treaty, International Search Report and Written Opinion, International Patent Application No. PCT/AU2007/001340, Nov. 1, 2007, 8 Pages.

Reynolds, et al. (2004) "Rational siRNA design for RNA interference," Nature Biotechnology, vol. 22, No. 3, pp. 326-330.

Robbins, M., et al., "Stable expression of shRNAs in human CD34+ progenitor cells can avoid induction of interferon responses to siRNAs in vitro," Nature Biotechnology, May 2006, pp. 566-571, vol. 24, No. 5.

Rose, S., et al., "Functional polarity is introduced by Dicer processing of short substrate RNAs," Nucleic Acids Research, 2005, pp. 4140-4156, vol. 33, No. 13.

Tuschl, T., "Functional genomics: RNA sets the standard," Nature, Jan. 16, 2003, vol. 421, No. 6920, pp. 220-221.

Tuschl T., "RNA Interference and Small Interfering RNAs" Chembiochem, 2001, pp. 239-245, vol. 2.

Tuschl, T., et al., "Small Interfering RNAs: A Revolutionary Tool for the Analysis of Gene Function and Gene Therapy," Molecular Interventions, 2002, pp. 158-167, vol. 2, No. 3.

Tuschl, T., "Mammalian RNA Interference," RNAi, A Guide to Gene Silencing, Chapter 13, G.J. Hannon (ed,), 2003, pp. 265-295.

Tuschl, T., et al., "Targeted mRNA Degradation by Double-Stranded RNA In Vitro," Genes & Development, 1999, pp. 3191-3197, vol. 13.

Tuschl, T., "Expanding small RNA interference," Nature Biotechnology, May 2002, pp. 446-448, vol. 20.

Vickers, T., et al., "Efficient Reduction of Target RNAs by Small Interfering RNA and RNase H-dependent Antisense Agents," The Journal of Biological Chemistry, Feb. 28, 2003, pp. 7108-7118, vol. 278, No. 9.

Weil, et al (2002) "Targeting the Kinesin Eg5 to Monitor siRNA Transfection in Mammalian Cells," Biotechniques 33(6):1244-1248.

Zimmerman, et al. (2006) "RNAi-mediated gene silencing in non-human primates," Nature, vol. 441, May 4: 111-114.

European Patent Office, Communication Pursuant to Article 94(3) EPC, European Patent Application No. 07 800 294.6, Oct. 5, 2012, 7 Pages.

European Patent Office, Communication Pursuant to Article 94(3) EPC, European Patent Application No. 07800294.6, Apr. 29, 2013, 6 Pages.

Patent Examination Report No. 1 for Australian Patent Application No. 2007344641, Aug. 14, 2012, 4 pages.

Hornung, V., et al., "Sequence-specific potent induction of IFN-α by short interfering RNA in plasmacytoid dendritic cells through TLR7," Nature Medicine, Mar. 2005, pp. 263-270, vol. 11, No. 3.

* cited by examiner

Figure 2 (normal mice with TC-1 cells)
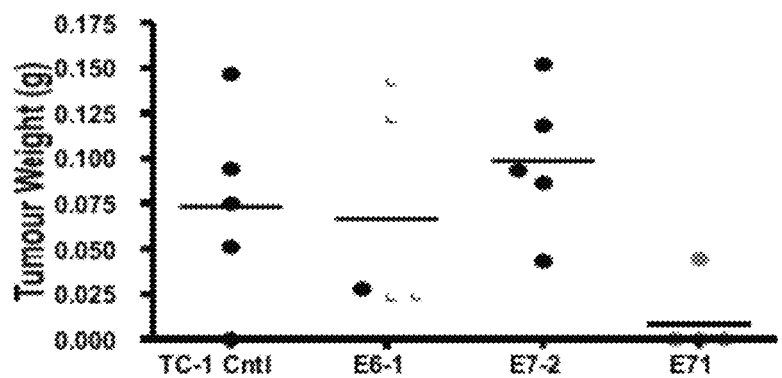
Figure 3
A  (Rag-/- mice with TC-1 cells)
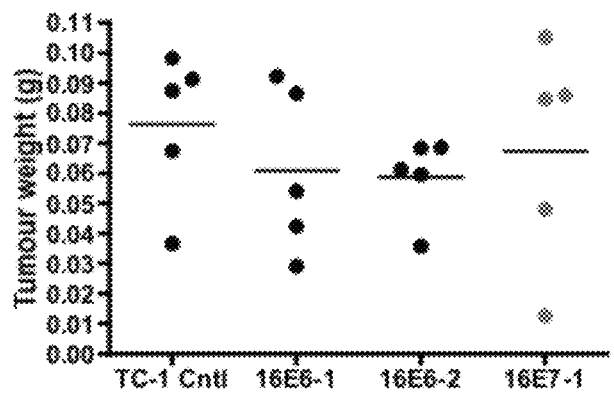
B  (normal mice with C2 tumour cells)
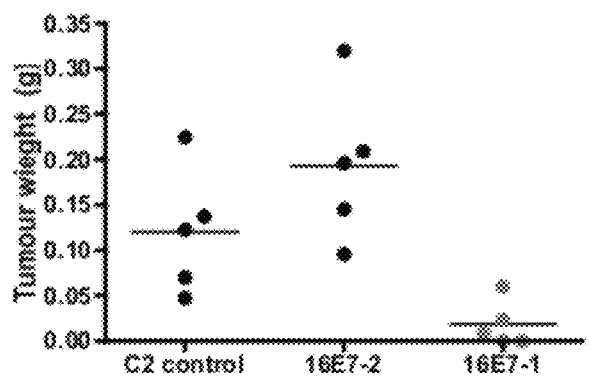

Figure 4
A
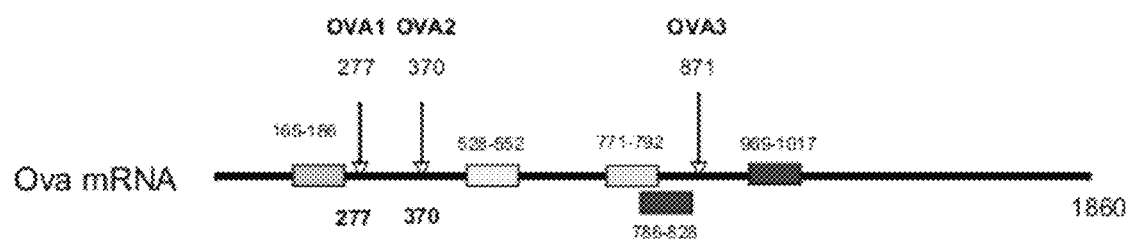
B
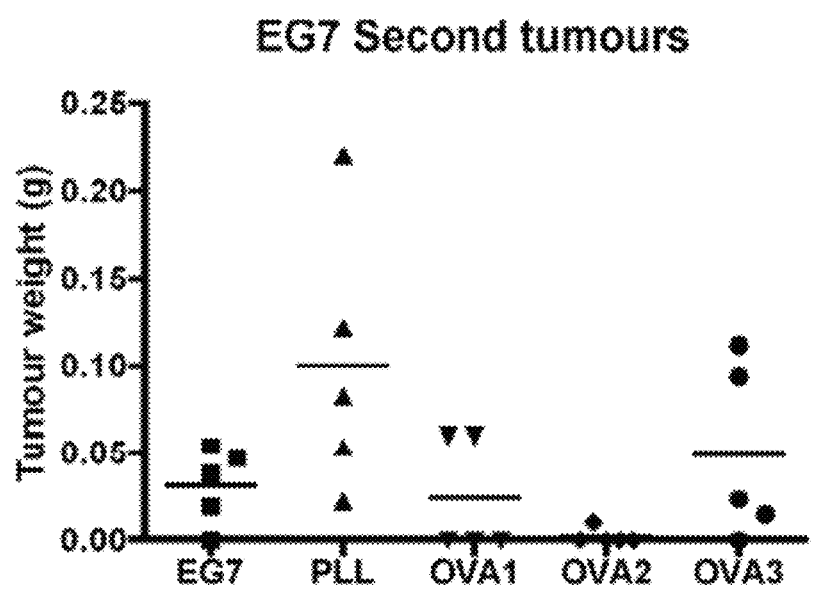

METHOD OF INDUCING AN IMMUNE RESPONSE

CROSS-REFERENCE TO RELATED APPLICATIONS

This application is a divisional application of U.S. patent application Ser. No. 11/900,412, filed on Sep. 11, 2007, which claims the benefit of U.S. Provisional Patent Application No. 60/880,547, filed Jan. 16, 2007, the disclosures of each of which are incorporated herein by reference.

REFERENCE TO SEQUENCE LISTING

The instant application contains a Sequence Listing, which has been submitted via EFS-Web and is hereby incorporated by reference in its entirety. Said ASCII copy, created on Jun. 21, 2012, is named 21272_US_CRF_sequence_listing.txt, lists 22 sequences, and is 20,222 bytes in size.

FIELD OF THE INVENTION

The present invention relates to methods for inducing or enhancing the immune response in a mammal. In particular, the invention relates to a method for inducing or enhancing the T cell mediated immune response in a mammal. This invention also relates to pharmaceutical compositions comprising inhibitory nucleic acids.

BACKGROUND TO THE INVENTION

RNA interference (RNAi) is a form of post-transciptional gene silencing mediated by short non-coding RNA molecules. RNAi is thought to act via specific base pairing with complementary target nucleic acid resulting in the degradation of the target molecule or inhibition of its translation. There are a wide range of RNA classes and pathways that can result in down-regulation or gene silencing.

Previous studies have shown that inhibitory RNA molecules may be useful in the treatment of certain diseases, including cancer. These studies have focused on directly killing tumour cells by silencing particular genes involved in cancer maintenance and development. However, to be effective, the inhibitory RNA molecules must be delivered and expressed at a cytotoxic level in each tumour or disease cell. Accordingly, very large dosages of inhibitory RNA molecules need to be administered to achieve a reasonable amount of tumour reduction or disease control. Very little success has been achieved in the effective reduction of tumour cells or disease using this method.

Accordingly, there is a need for improved methods for effectively using inhibitory nucleic acids to treat disease, that do not necessarily rely on large dosages of the inhibitory nucleic acid or direct killing of every target cell to be effective.

SUMMARY OF THE INVENTION

It has now been found that targeting inhibitory nucleic acid molecules to specific regions of an RNA encoding a polypeptide of interest can lead to the induction of a T cell response in an individual against the polypeptide. Specifically, the inhibitory nucleic acid molecule is targeted to a particular region of the RNA which encodes the target polypeptide of interest, such that an aberrant, e.g. truncated, form of that protein is expressed which comprises at least one T cell epitope The aberrant form of the target polypeptide is processed by the cell and at least a part thereof comprising a T cell epitope is presented on the cell surface in combination with an MHC class molecule for recognition by a T cell. This results in an immune response against the polypeptide leading to the death of cells that present part of the polypeptide comprising a T cell epitope on the cell surface.

Accordingly in a first aspect the present invention provides a method of inducing or enhancing an immune response in a mammal to a target polypeptide expressed in a plurality of cells of the mammal, which method comprises administering to the mammal an inhibitory nucleic acid which targets a region of a ribonucleic acid (RNA) which encodes said polypeptide such that translation of a defective or aberrant form of the target polypeptide occurs in said cells, said defective or aberrant form of the target polypeptide comprising one or more T cell epitopes.

In a related aspect, the present invention provides a method of inducing or enhancing an immune response in a mammal to a target polypeptide expressed in a plurality of cells of the mammal, which method comprises administering to the mammal an inhibitory nucleic acid which targets a region of a ribonucleic acid (RNA) which encodes said polypeptide such that translation of a defective or aberrant form of the target polypeptide occurs in said cells, said defective or aberrant form of the target polypeptide comprising one or more T cell epitopes and wherein at least a part of the polypeptide comprising a T cell epitope is presented on the cell surface.

The present invention also provides a method of inducing or enhancing an immune response in a mammal to a target polypeptide expressed in a plurality of cells of the mammal, which method comprises administering to the mammal an inhibitory nucleic acid which targets a region of an RNA which encodes said polypeptide, such that at least a portion of the polypeptide, which portion comprises a T cell epitope, is presented on the surface of the cells bound to major histocompatibility complex (MHC).

In a second aspect of the invention there is provided a method of killing tumour cells in a patient which method comprises administering to the patient an inhibitory nucleic acid which targets a region of an RNA which encodes a target polypeptide expressed in said tumour cells of the patient, such that translation of a defective or aberrant form of the target polypeptide, comprising one or more T cell epitopes, occurs in said cells.

In a related aspect of the invention there is provided a method of killing tumour cells in a patient which method comprises administering to the patient an inhibitory nucleic acid which targets a region of an RNA which encodes a target polypeptide expressed in said tumour cells of the patient, such that translation of a defective or aberrant form of the target polypeptide, comprising one or more T cell epitopes, occurs in said cells and wherein at least a part of the polypeptide comprising a T cell epitope is presented on the cell surface.

The present invention also provides a method of killing tumour cells in a patient which method comprises administering to the patient an inhibitory nucleic acid which targets a region of an RNA which encodes a target polypeptide expressed in said tumour cells of the patient, such that at least a portion of the polypeptide, which portion comprises a T cell epitope, is presented on the cell surface bound to MHC.

In one embodiment the target polypeptide is an endogenous polypeptide expressed by the tumour cells. In another embodiment the target polypeptide is a viral polypeptide expressed by a virus present in the tumour cells.

In a third aspect the present invention provides a method of treating a disease caused by an intracellular pathogen, such as a virus, which method comprises administering to a patient suffering from said disease an inhibitory nucleic acid which targets a region of an RNA which encodes a target polypeptide expressed by the pathogen in cells of the patient, such that translation of a defective or aberrant form of the target polypeptide, comprising one or more T cell epitopes, occurs in said cells.

In a related aspect the present invention provides a method of treating a disease caused by an intracellular pathogen, such as a virus, which method comprises administering to a patient suffering from said disease an inhibitory nucleic acid which targets a region of an RNA which encodes a target polypeptide expressed by the pathogen in cells of the patient, such that translation of a defective or aberrant form of the target polypeptide, comprising one or more T cell epitopes, occurs in said cells and wherein at least a part of the polypeptide comprising a T cell epitope is presented on surface of the cells.

The present invention also provides a method of treating a disease caused by an intracellular pathogen which method comprises administering to a mammal suffering from said disease an inhibitory nucleic acid which targets a region of an RNA which encodes a target polypeptide expressed by the pathogen in cells of the mammal, such that at least a portion of the polypeptide, which portion comprises a T cell epitope, is presented on the cell surface bound to MHC.

In a fourth aspect of the invention there is provided a pharmaceutical composition comprising an inhibitory nucleic acid which targets a region of an RNA which encodes a target polypeptide expressed in a plurality of cells of a mammal, such that translation of a defective or aberrant form of the target polypeptide occurs in said cells, said defective or aberrant form of the target polypeptide comprising one or more T cell epitopes, together with a pharmaceutically acceptable carrier or diluent.

In a related aspect of the invention there is provided a pharmaceutical composition comprising an inhibitory nucleic acid which targets a region of an RNA which encodes a target polypeptide expressed in a plurality of cells of a mammal, such that translation of a defective or aberrant form of the target polypeptide occurs in said cells, said defective or aberrant form of the target polypeptide comprising one or more T cell epitopes and wherein at least a part of the polypeptide comprising a T cell epitope is presented on the cell surface, together with a pharmaceutically acceptable carrier or diluent.

The present invention also provides a pharmaceutical composition comprising an inhibitory nucleic acid which targets a region of an RNA which encodes a target polypeptide expressed in a plurality of cells of a mammal, such that at least a portion of the polypeptide, which portion comprises a T cell epitope, is presented on the cell surface bound to MHC, together with a pharmaceutically acceptable carrier or diluent.

The present invention also provides the pharmaceutical composition of the invention for use in treating cancer or in treating a disease caused by an intracellular pathogen, such as a virus.

Preferably in the various aspects of the invention described above, at least one T cell epitope is a cytotoxic T lymphocyte (CTL) epitope.

In one embodiment of the various aspects of the invention described above, the target polypeptide is a tumour antigen. The tumour antigen may, for example, be a polypeptide which is foreign to the cell, or an endogenous protein.

In an alternative embodiment the target polypeptide is a viral polypeptide, such as an oncogenic viral polypeptide e.g. human papilloma virus E6 or E7.

Preferably, the dose of the inhibitory nucleic acid administered is insufficient to kill directly the cells expressing the target protein.

In a preferred embodiment the inhibitory nucleic acid is an RNAi agent, e.g. an interfering RNA, such as an siRNA or shRNA.

DETAILED DESCRIPTION OF THE INVENTION

Unless defined otherwise, all technical and scientific terms used herein have the same meaning as commonly understood by one of ordinary skill in the art (e.g. in cell biology, chemistry and molecular biology). Standard techniques used for molecular and biochemical methods can be found in Sambrook et al., Molecular Cloning: A Laboratory Manual, $3^{rd}$ ed. (2001) Cold Spring Harbor Laboratory Press, Cold Spring Harbor, N.Y. and Ausubel et al., Short Protocols in Molecular Biology (1999) $4^{th}$ Ed, John Wiley & Sons, Inc.—and the full version entitled Current Protocols in Molecular Biology). See also RNA Interference Technology: From Basic Science to Drug Development, 2005, Ed Krishnarao Appasani, Cambridge University Press, UK.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Throughout this specification, reference to numerical values, unless stated otherwise, is to be taken as meaning "about" that numerical value. The term "about" is used to indicate that a value includes the inherent variation of error for the device and the method being employed to determine the value, or the variation that exists among the study subjects.

Inhibitory Nucleic Acids

The term "inhibitory nucleic acid" as described herein means a nucleic acid that binds to an mRNA that encodes a polypeptide of interest and inhibits translation of the full length polypeptide encoded by the mRNA. Previously inhibitory nucleic acids have been used to try to silence gene expression and therefore the inhibitory nucleic acids used were intended to prevent translation occurring altogether. By contrast, in the context of the present invention, inhibitory nucleic acid molecules are selected which allow at least some translation of a defective or aberrant polypeptide, such as a C-terminally truncated polypeptide. Preferably, the inhibitory nucleic acid permits expression of a defective or aberrant polypeptide in cells at a level of at least 10% (in terms of number of polypeptide molecules) of normal levels in the absence of the inhibitory nucleic acid, more preferably at least 20, 30, 40 or 50%. This can be tested in vitro using suitable cell lines.

Nucleic acids may be RNA or DNA or analogs or derivatives thereof. Nucleic acids may be double-stranded, single-stranded, linear, circular, synthetic, recombinantly produced, as well as altered nucleic acids that differ from naturally occurring RNA or DNA by the addition, deletion, substitution and/or alteration of one or more nucleotides. Such alterations can include addition of non-nucleotide material, such as to the end(s) of the nucleic acid or internally. Nucleotides in the nucleic acid molecules of the present invention can also comprise non-standard nucleotides, such as non-naturally occurring nucleotides or chemically synthesized nucleotides or deoxynucleotides, especially those that enhance the in vivo stability and/or pharmacokinetics of the nucleic acid molecules.

The inhibitory nucleic acid may be capable of giving rise directly to an inhibitory effect, subject to processing by cellular machinery where appropriate, or it may be in the form of a vector which expresses such a nucleic acid, e.g. a viral vector or plasmid. Viral vectors includes lentiviral vectors.

Typically, the inhibitory nucleic acid is an RNA interference agent (RNAi agent) or a nucleic acid vector that expresses or otherwise gives rise to an RNAi agent (e.g. a DNA-directed RNAi (ddRNAi) agent—see US Patent Application Publication No. 2006/0115455). RNA interference (RNAi) is a form of post-transcriptional gene silencing mediated by small non-coding RNA molecules of approximately 15 to 30 nucleotides in length. There are a wide range of RNA classes and pathways that can result in down-regulation of gene expression or gene silencing. In mammalian cells, RNAi can be triggered by 21-nucleotide (nt) duplexes of short interfering RNA or by micro-RNAs (miRNA), or other dsRNAs. Functional small-hairpin RNAs (shRNA) have an added stem-loop structure which is cleaved to form short interfering RNAs.

Thus, the term RNAi agent is intended to encompass other terms used to describe nucleic acid molecules that are capable of mediating sequence specific RNAi, for example double-stranded RNA (dsRNA), micro-RNA (miRNA), short hairpin RNA(shRNA), chemically-modified sRNA, post-transcriptional gene silencing RNA (ptgsRNA), and others.

The inhibitory nucleic acid can be a polynucleotide with a duplex, asymmetric duplex, hairpin or asymmetric hairpin secondary structure, having self-complementary sense and antisense regions. The inhibitory nucleic acid may also be a circular single-stranded polynucleotide having two or more loop structures and a stem comprising self-complementary sense and antisense regions, wherein the circular polynucleotide can be processed either in vivo or in vitro to generate an active inhibitory nucleic acid molecule capable of mediating RNAi. The inhibitory nucleic acid can also be generated by cleavage of longer dsRNA with RNase III or Dicer. These enzymes process the dsRNA into biologically active siRNA (see, e.g., Yang et al., PNAS USA 99: 9942-7 (2002); Calegari et al., 2002, PNAS USA 99: 14236; Byrom et al., 2003, Ambion TechNotes 10(1): 4-6; Kawasaki et al., 2003, Nucleic Acids Res. 31: 981-7; Knight and Bass, 2001, Science 293: 2269-71; and Robertson et al., 1968, J. Biol. Chem. 243: 82).

In one embodiment, the inhibitory nucleic acid can be a double-stranded polynucleotide molecule comprising self-complementary sense and antisense regions. The inhibitory nucleic acid can be assembled from two separate oligonucleotides, where one strand is the sense strand and the other is the antisense strand.

Alternatively, the inhibitory nucleic acid may be assembled from a single oligonucleotide, where the self-complementary sense and antisense regions of the inhibitory nucleic acid are linked by means of a nucleic acid based or non-nucleic acid-based linker(s), e.g. shRNA. Inhibitory nucleic acids of the present invention may have one or more stem-loop structures where the ends of the double-stranded RNA are connected by a single-stranded, linker RNA. The length of the single-stranded loop portion of is typically from about 5 to 20 nucleotides in length, such as from about 5 to 11 nucleotides in length.

The double-stranded portions of inhibitory nucleic acid molecules may be completely homologous, or may contain non-paired portions due to sequence mismatch (the corresponding nucleotides on each strand are not complementary), bulge (lack of a corresponding complementary nucleotide on one strand), and the like. Such non-paired portions can be tolerated to the extent that they do not significantly interfere with duplex formation or efficacy.

In a particular embodiment of the invention, the inhibitory nucleic acid, such as an RNAi agent, may be from about 15 to 60, 15 to 50, or 15 to 40 (duplex) nucleotides in length, such as from about 15 to 30, 15 to 25 or 19 to 25 (duplex) nucleotides in length, e.g. from about 20 to 24 or from about 21 to 23 or 21 to 22 (duplex) nucleotides in length. Nucleic acid duplexes may comprise 3' overhangs of from about 1 to about 4 nucleotides, preferably about 2 or 3 nucleotides, and 5' phosphate termini.

As mentioned above, the inhibitory nucleic acids of the invention can include both naturally-occurring polynucleotides and analogues or derivatives thereof, e.g.

siRNAs modified to alter a property such as the pharmacokinetics of the composition. Examples of suitable modifications include those that increase half-life of the nucleic acid in the body, increase shelf-life, stability, and ease of introduction to the target site, e.g., to enhance penetration of cellular membranes, and confer the ability to recognise and bind to targeted cells. Examples of modifications that are contemplated include; the use of locked nucleic acid analogues and 2'-0-Methyl RNA bases. Other modifications are described in US Patent Application Publication No. 2006/0115455, the relevant sections of which are herein incorporated by reference.

The inhibitory nucleic acid molecules of the invention may be designed using any suitable method known in the art: a number of algorithms are known, and are commercially available (e.g. Cenix BioScience GmbH, Dresden, Germany; Dharmacon Inc., CO, USA; Qiagen Inc., Valenica, Calif., USA; and Ambion Inc., Tex., USA). However, unlike previous approaches to RNAi, the present invention is based on allowing at least some translation to occur of target polypeptides rather than attempting to silence translation of the target polypeptide. It is believed that by targeting regions of the mRNA downstream of regions encoding T cell epitopes, the resulting expressed polypeptides comprising at least one T cell epitope, are recognised by cellular machinery as defective or aberrant e.g. as a result of misfolding, and are targeted for destruction in the cell's proteasomes leading to presentation of peptides derived from the polypeptide by MHC molecules on the surface of the cell which exposes the peptides to recognition by T cells.

Accordingly, inhibitory nucleic acid molecules of, and for use in, the present invention will generally be designed such that the resulting binding moieties (e.g. siRNAs) are complementary to a region of the mRNA which encodes the target polypeptide, which region is 3' of a region of the mRNA encoding a T cell epitope, such as a major/immunodominant CTL or helper T cell epitope, a subdominant CTL or helper T cell epitope or a cryptic CTL or helper T cell epitope.

The optimal distance between the 3' end of the mRNA region encoding the T cell epitope and the region to which the inhibitory nucleic acid binds for a given polypeptide and inhibitory nucleic acid construct can be determined by experimentation using a range of constructs.

In one embodiment, the distance between the 3' end of the mRNA region encoding the T cell epitope and the region to which the inhibitory nucleic acid binds is relatively small, i.e. less than about 100 nucleotides, such as less than about 90, 80, 70, 60 or 50 nucleotides, such as less than 40, 30 or 20 nucleotides. In this embodiment, the distance between the 3' end of the mRNA region encoding the CTL epitope and the region to which the inhibitory nucleic acid binds may be at least about 5 nucleotides, such as at least 10, 15 or 20 nucleotides.

In another embodiment, the distance between the 3' end of the mRNA region encoding the T cell epitope and the region to which the inhibitory nucleic acid binds is greater, being more than about 50 nucleotides, such as more than about 60, 70, 80, 90 or 100 nucleotides. In this embodiment, the distance between the 3' end of the mRNA region encoding the CTL epitope and the region to which the inhibitory nucleic acid binds is typically less than about 500 nucleotides, such as at least 10, 15 or 20 nucleotides.

The sequences for the inhibitory nucleic acid molecules, e.g. RNAi agent or agents, are selected based upon the nucleotide sequence of the target sequence(s). For example, sequences may be are based on regions of the target sequences that are conserved, or alternatively on regions that are unique to the target sequence to avoid inhibition of related sequences that it is not desired to target.

Methods of alignment of sequences for comparison and RNAi sequence selection are well known in the art. The determination of percent identity between two or more sequences can be accomplished using a mathematical algorithm.

Computer implementations of these mathematical algorithms include, but are not limited to: CLUSTAL in the PC/Gene program (available from Intelligenetics, Mountain View, Calif.); the ALIGN program (Version 2.0), GAP, BESTFIT, BLAST, FASTA, Megalign (using Jotun Hein, Martinez, Needleman-Wunsch algorithms), DNAStar Lasergene (see www.dnastar.com) and TFASTA in the Wisconsin Genetics Software Package, Version 8 (available from Genetics Computer Group (GCG), 575 Science Drive, Madison, Wis., USA). Alignments using these programs can be performed using the default parameters or parameters selected by the operator. Software for performing BLAST analyses is publicly available through the National Center for Biotechnology Information (http://www.ncbi.nlm.nih.gov/).

Typically, inhibition of target sequences by inhibitory nucleic acid molecules requires a high degree of sequence identity between the target sequence and the sense strand of the inhibitory nucleic acid molecules. In some embodiments, such identity is greater than about 70%, and may be greater than about 75%. Preferably, identity is greater than about 80%, and is greater than 85% or even 90%. More preferably, sequence identity between the target sequence and the sense strand of the inhibitory nucleic acid molecules is greater than about 90%, 91%, 92%, 93%, 94%, 95%, 96%, 97%, 98% or 99%.

In addition to designing inhibitory nucleic acid molecule sequences based on conserved or unique regions of a target sequence, design and selection of the inhibitory nucleic acid molecule sequences may be based on other factors. However, although various selection criteria based on features of the desired target sequence can assist in RNAi design (e.g. percent GC content, position from the region encoding a T cell epitope, sequence similarities based on an in silico sequence database search for homologues of the proposed RNAi agent, and thermodynamic pairing criteria), individual, specific, candidate inhibitory nucleic acid sequences are typically tested in vitro or in vivo to confirm that interference with expression of a desired target can be elicited (in this case expression of defective, e.g. truncated, polypeptide and/or presentation of peptides derived from the target polypeptide on the cell surface rather than silencing) or via functional testing of elicitation of an immune response, which can be tested by immunizing mice with inhibitory nucleic acid-treated tumour cells and challenging with untreated tumour cells and observing if reduction in tumour size occurs. One could also observe if tumour-specific antibodies or CTLs are generated by such immunizations.

In some embodiments, a plurality of inhibitory nucleic acid molecules may be designed which target different regions of the mRNA.

Inhibitory nucleic acid molecules are typically made either synthetically using standard techniques, such as solid phase synthesis, which enables the use of non-naturally occurring nucleotides, or recombinantly using nucleic acid vectors.

In embodiments where interfering RNA is used, the relevant RNA transcription units can be incorporated into a variety of vectors for introduction into target cells.

For example, suitable vectors include, but are not restricted to, plasmid DNA vectors, viral DNA vectors (such as adenovirus or adeno-associated virus vectors), or viral RNA vectors (such as retroviral or alphavirus vectors). The expression vector can encode an RNAi agent sequence that can self assemble upon expression from the vector into a duplex oligonucleotide. The RNAi agent can, for example, be transcribed as sequences that automatically fold into duplexes with hairpin loops from DNA templates in plasmids. Recombinant DNA constructs using bacterial or mammalian promoter systems (e.g. U6/snRNA promoter systems) can be used. The selected promoter can provide for constitutive or inducible transcription. Plasmids suitable for in vivo delivery of genetic material for therapeutic purposes are described in detail in U.S. Pat. Nos. 5,962,428 and 5,910,488. It will be apparent to those of skill in the art that vectors originally designed to express desired gene sequences can be modified to contain a transcriptional unit cassette for transcription of an RNAi agent.

RNAi agent-expressing vectors can be constructed based on, but not limited to, adeno-associated virus, retrovirus, adenovirus, alphavirus or lentivirus plasmid as well as other known vectors. The recombinant vectors capable of expressing the RNA molecules can be delivered to target cells. Such vectors can be repeatedly administered as necessary. Alternatively, certain RNA molecules can be expressed within cells from eukaryotic promoters.

Target Polypeptides

The term "polypeptide" includes peptides of two or more amino acids in length, typically having more than 5, 10 or 20 amino acids. The term "protein" includes single-chain polypeptide molecules as well as multiple-polypeptide complexes where individual constituent polypeptides are linked by covalent or non-covalent means.

The term "target polypeptide" refers to any polypeptide expressed in a mammalian cell against which it is desired to generate an immune response. The target polypeptide can be endogenous or foreign to the mammalian cell. Endogenous polypeptides include tumour antigens. The term "endogenous" means that the polypeptide is encoded by the genome of the host cell.

Foreign polypeptides, conversely, are polypeptides that are not encoded by the genome of the host cell, such as polypeptides expressed by intracellular pathogens such as viruses and some mycoplasma. The definition of "foreign polypeptide" in this context is also taken to include polypeptides not encoded by the germ line genome of the host mammal but which result from mutations in the host cell, such as insertions, deletions, substitutions and/or translocations.

In one embodiment, the target polypeptide is an endogenous polypeptide involved in cancer development, maintenance or spread, such a cellular oncogenic polypeptide.

In another embodiment, the target polypeptide is a foreign polypeptide, such as a viral polypeptide, involved in cancer development, maintenance or spread e.g. a human papillomavirus (HPV) E6 or E7 polypeptide.

Other suitable target polypeptides include viral polypeptides, such as those associated with viral infection and survival; proteins associated with metabolic diseases and disorders; polypeptides associated with tumourigenesis, tumour migration and cell transformation, angiogenesis, immunomodulation, such as those associated with inflammatory and autoimmune responses, and polypeptides associated with neurodegenerative disorders.

Polypeptides associated with viral infection and survival may include those expressed by a virus in order to bind, enter and replicate in a cell. Of particular interest are viral sequences associated with chronic viral diseases, for example hepatitis viruses, human immunodeficiency viruses (HIV), herpes viruses, human papillomaviruses (HPV), Epstein Barr viruses (EBV) and human T-cell lymphotropic virus type I and II (HTLV I, HTLV II).

Other target polypeptides that are suitable for use with the present invention are mycoplasma polypeptides and other pathogen-related polypeptides.

Target polypeptides are those which are capable of giving rise to an immune response following cellular processing and presentation. Accordingly, target polypeptides typical comprise one or more T cell epitopes.

T cell epitopes can be divided into two classes: cytotoxic T cell epitopes and helper T cell epitopes. Cells infected with viruses or bacteria that exist in the cytosol are targeted by cytotoxic T cells. Cytotoxic T cells are characterised by the presence of a cell surface molecule known as CD8. A different class of T cells detects pathogens and their products which exist in vesicular compartments of the cell. These are known as helper T cells. This class of T cells is identified by the expression of the CD4 cell surface molecule. Thus the term "T cell" is intended to refer to both CD8 and CD4 characterised T cells, and the term "T cell epitope" refers to epitopes recognised by such T cells, i.e. CTL epitopes, which are presented on the cell surface bound to major histocompatibility complex (MHC) class I proteins, as well as helper T cell epitopes which are presented on the cell surface bound to MHC class II proteins.

Foreign antigens are processed by antigen presenting cells and presented on the cell surface by major histocompatibility complex (MHC) proteins. As discussed above, T cells such as CTLs and helper T cells express receptors (CD8 or CD4, respectively) that recognise an antigen bound to MHC on an antigen presenting cell. The CTLs, for example, then secrete certain molecules which result in the death of the infected cells. Whether a certain antigen is able to trigger a T cell response is dependent on the presence and the nature of the T cell epitope in that antigen. T cell epitopes can vary in size and are present in endogenous proteins and also foreign proteins, such as viral proteins. For example, a CTL epitope is known to exist in the E7 gene of HPV. T cell epitopes have been identified for a range of polypeptides. In addition, methods and techniques for mapping the frequency and distribution of T cell epitopes within a particular polypeptide sequence have been developed (see, for example, Moutaftsi, 2006, Nat. Biotechnol. 24; 817-819).

Target polypeptides may comprise a plurality of T cell epitopes. However, typically where multiple T cell epitopes exist in a given polypeptide, one of the epitopes induces a stronger T cell response than the others. Such a T cell epitope is herein termed a "major" T cell epitope (or an "immunodominant" epitope). Also typically, where multiple T cell epitopes exist in a given polypeptide, one or more epitopes may be considered to be a sub-dominant T cell epitope. T cell epitopes may also be "cryptic" epitopes (i.e. epitopes which are not exposed in the full length native polypeptide but which are revealed, for example, in fragments of the full length polypeptide).

Preferably at least one T cell epitope is a cytotoxic T lymphocyte (CTL) epitope.

As mentioned above, the inhibitory nucleic acid molecules of the invention are designed to target a region of an RNA, typically an mRNA, which encodes the target polypeptide, such that translation of an aberrant, e.g. truncated, form of the target polypeptide occurs in the host cells. The phrase, "target a region of an RNA" means that the inhibitory nucleic acid (or a product thereof following transcription and/or intracellular processing) binds to a region of the RNA and interferes with translation of the RNA. Binding generally occurs by sequence-specific interaction between the inhibitory nucleic acid and the complementary target sequence within the target RNA. Accordingly, the inhibitory nucleic acids of the invention are designed to interact with the target region of the RNA to create the desired effect.

In one embodiment, the inhibitory nucleic acids of the invention are targeted to a region of an RNA such that, as a result of the interaction of the inhibitory nucleic acid and the target RNA, one or more aberrant, e.g. truncated, forms of the polypeptide encoded by the RNA is produced, said aberrant, e.g. truncated, form of the target polypeptide comprising one or more T cell epitopes, preferably at least one major T cell epitope, such as a major CTL epitope.

Preferably, the aberrant form of the target polypeptide is processed by the cell and at least a part thereof comprising a T cell epitope is presented on the cell surface in combination with an MHC class molecule for recognition by a T cell, preferably a CTL.

In one embodiment, the one or more T cell epitopes in the aberrant, e.g. truncated, polypeptide include at least one major/immunodominant CTL epitope (with respect to the full length polypeptide).

In one embodiment, the one or more T cell epitopes in the aberrant polypeptide include at least one sub-dominant or cryptic T cell epitope (with respect to the full length polypeptide).

In some embodiments, a plurality of inhibitory nucleic acid molecules may be used which target different regions of the mRNA. For example, different constructs may bind downstream of different T cell epitope-encoding portions of the mRNA to generate truncated polypeptides of differing length with different T cell epitopes proximal to the C-terminus of the truncated polypeptide.

Applications

Without wishing to be bound by theory, it is believed that aberrant (e.g. truncated) target polypeptides expressed as a result of the effect of inhibitory nucleic acid molecules in the cell may be recognised as defective, e.g. misfolded, and sent to the cellular protein degradation machinery for processing. When the resulting fragments of the target protein are captured by the MHC complex and presented on the cell surface, a T cell-mediated immune response may occur, depending on the ability of the presented peptides to induce such a response. This leads to the activation of T cells and the destruction of cells presenting the antigen of interest. Thus, the elevated presence of aberrant, e.g. truncated, target polypeptides in the cells is believed to increase immune presentation and therefore induce or enhance the T cell immune response against these target peptides in the individual.

Accordingly the present invention provides a method of inducing or enhancing an immune response in a mammal to a target polypeptide expressed in a plurality of cells of the mammal, which method comprises administering to the mammal an inhibitory nucleic acid which targets a region of a ribonucleic acid (RNA) which encodes said polypeptide.

The term mammal includes primates, such as humans, ungulates, cats, dogs, rodents and the like.

The present invention also provides a method of killing tumour cells in a mammal which method comprises administering to the mammal an inhibitory nucleic acid which targets a region of an RNA which encodes a target polypeptide expressed in said tumour cells of the mammal, such that translation of an aberrant, preferably truncated, form of the target polypeptide, comprising one or more T cell epitopes, occurs in said cells.

Thus the methods of the invention can be used to treat cancers and other malignancies where a target polypeptide can form the basis for an immune response against tumour cells expressing the polypeptide.

The present invention also provides a method of treating a disease caused by an intracellular pathogen which method comprises administering to a mammal suffering from said disease an inhibitory nucleic acid which targets a region of an RNA which encodes a target polypeptide expressed by the pathogen in cells of the mammal, such that at least a portion of the polypeptide, which portion comprises a T cell epitope, is presented on the cell surface bound to MHC.

Intracellular pathogens include viruses and some mycoplasma.

The term "disease" refers to any deviation from the normal health of a mammal and includes a state when disease symptoms are present, as well as conditions in which a deviation (e.g., infection, gene mutation, genetic defect, etc.) have occurred, but symptoms have not yet manifested.

The routes of administration and dosages described are intended only as a guide since a skilled practitioner will be able to determine readily the optimum route of administration and dosage for any particular patient and condition.

Delivery

Methods for the delivery of nucleic acid molecules to mammalian cells, including therapeutic delivery, are known in the art and are described in, for example, Akhtar et al., 1992, Trends Cell Biol. 2: 139; Delivery Strategies for Antisense Oligonucleotide Therapeutics, ed. Akhtar, 1995, Maurer et al., 1999, Mol. Membr. Biol.: 16, 129-140; pill form) and/or intrathecal delivery (Gold, 1997, Neuroscience, 76, 1153-1158). See also RNA Interference Technology: From Basic Science to Drug Development, 2005, Ed Krishnarao Appasani, Cambridge University Press, UK.

According to the method of the invention, the inhibitory nucleic acids can be administered directly to target cells or tissues, or can be complexed with cationic lipids, neutral lipids, packaged within liposomes, or polymeric nanoparticles, or otherwise delivered to target cells or tissues. Examples of other such complexes include, but are not limited to, small molecules, lipids, cholesterol, phospholipids, nucleosides, nucleotides, nucleic acids, antibodies, toxins, negatively charged polymers and other polymers, for example, proteins, peptides, hormones, carbohydrates, polyethylene glycols, or polyamines, across cellular membranes.

In another embodiment, polyethylene glycol (PEG) is covalently attached to the compounds of the present invention. The attached PEG can be any molecular weight but is preferably between 2000-50,000 daltons.

In one embodiment, the inhibitory nucleic acids can be locally administered to relevant tissues ex vivo, or in vivo for example, through injection, infusion pump, spray or a stent.

In another embodiment, the inhibitory nucleic acids can be delivered by systemic administration (e. g. by injection, such as subcutaneous, intravenous, topical administration, or the like) to a tissue or cell in a subject; or by administration to target cells explanted from a subject followed by reintroduction into the subject, or by any other means that would allow for introduction into the desired target cell (ex vivo therapy).

The term "systemic administration" refers to in vivo systemic absorption or accumulation in the blood stream followed by distribution throughout the entire body.

Administration routes that lead to systemic absorption include, without limitation: intravenous, subcutaneous, intraperitoneal, inhalation, oral, intrapulmonary and intramuscular.

Typically, the inhibitory nucleic acids of the invention are combined with a pharmaceutically acceptable carrier or diluent, with or without stabilizers, buffers, and the like, to form a pharmaceutical composition. Suitable pharmaceutical carriers are described in "Remington's Pharmaceutical Sciences" by E. W. Martin. When liposome delivery is used, standard protocols for formation of liposomes can be followed.

The term "pharmaceutical composition" refers to a composition or formulation that allows for the effective distribution of the inhibitory nucleic acid molecules of the present invention in the physical location most suitable for their desired activity.

Suitable forms of the composition, in part, depend upon the use or the route of entry, for example oral, transdermal, or by injection. Such forms should not prevent the composition or formulation from reaching a target cell (i.e., a cell to which the negatively charged nucleic acid is desirable for delivery). For example, pharmaceutical compositions injected into the blood stream should be soluble. Other factors are known in the art, and include considerations such as toxicity and forms that prevent the composition or formulation from exerting its effect.

The pharmaceutical compositions of the present invention can also be formulated and used as tablets, capsules or elixirs for oral administration, suppositories for rectal administration, sterile solutions, powders for inhalation/nasal delivery, suspensions for injectable administration, and the other compositions known in the art.

A single dosage form of a pharmaceutical composition preferably comprises from about 1 mg to about 1 g of inhibitory nucleic acid molecules of the invention, preferably less than 100 mg. In the case of dosage forms intended for local delivery (such as mucosal delivery—e.g. pulmonary delivery such as nasal delivery) a single dosage form preferably comprises from about 1 µg to 1 g, preferably less than 100 mg, more preferably less than 10 or 1 mg.

In one embodiment, the pharmaceutical composition comprises a plurality of inhibitory nucleic acid molecules which target different regions of the mRNA encoding the target polypeptide.

Dosage

According to one embodiment of the present invention, an effective administration protocol comprises suitable dose parameters and modes of administration that result in delivery of the inhibitory nucleic acid in an amount that is suitable to induce or enhance the immune response of the subject to the target polypeptide. In another embodiment, an effective administration protocol comprises suitable dose parameters that result in the delivery of inhibitory nucleic acids in an amount suitable to kill tumour cells or diseased cells e.g. cells infected with a pathogen.

The induction or enhancement of an immune response in this manner can be an effective way of using an individual's own immune system to fight a disease or reduce tumour cell growth and spread. Since, by contrast to previous methods of RNA interference, cell death is based on inducing or enhancing an immune response to cells expressing the target polypeptide, it is not necessary for every target cell to express the inhibitory nucleic acid molecule at a level cytoxic to the cell. Thus, it is only necessary that sufficient expression of inhibitory nucleic acid molecules occurs in a sufficient number of cells to achieve the desired immune response, which in turn causes the death of target cells.

One of the difficulties to date with RNAi (and antisense technology) is that the techniques and constructs used are based on direct killing of cells by inhibiting of expression of target genes in those cells e.g. cellular oncogenes. It has proved difficult to deliver sufficient inhibitory nucleic acid molecules of sufficient efficacy to kill all targeted cells.

By contrast, since the present invention does not require direct killing of the cells, the dosage of inhibitory nucleic acid required to achieve the desired effect need not be at a level that is sufficient to directly cause the death of the cells expressing the target polypeptide. Accordingly, the dose of inhibitory nucleic acid may be reduced compared to conventional techniques.

Thus, in one embodiment, the inhibitory nucleic acid is not directly cytotoxic to the cells to which it is administered and/or is administered at a suitable dose that is insufficient to kill directly the cells expressing the target polypeptide.

The phrase "not directly cytotoxic" means that the inhibitory nucleic acid is not able to kill cells by a direct effect within the cell in which the inhibitory nucleic acid is expressed e.g. as a result of silencing expression of a gene critical for cell survival. The killing of cells via the generation of an immune response against the target polypeptide is herein defined as an indirect effect.

Similarly, the phrase "insufficient to kill directly the cells expressing the target polypeptide" means that the inhibitory nucleic acid is administered at a level where it is not directly cytotoxic to the cells by virtue of any gene silencing or gene down-regulation effects per se. Whether or not a particular inhibitory nucleic acid molecule is cytotoxic to cells expressing the target polypeptide (or is being administered at a cytotoxic dose) can be determined by suitable in vitro cellular assays and/or in vivo.

Accordingly, for the inventive methods and compositions to be effective, the inhibitory nucleic acids are not required to be present in an amount that would kill directly the cells in which they are expressed. Further, the inhibitory nucleic acids do not need to be present or expressed in each and every tumour or disease cell to be effective. Preferably the dosage of inhibitory nucleic acid is sufficient to lead to the induction or enhancement of the immune response to the target antigen. For example, a typical dose of inhibitory nucleic acids according to the present invention is from about 100 μg to about 10 mg per kilogram of body weight for systemic delivery, preferably less than 1 mg per kg of body weight e.g. less than 0.5, 0.2 or 0.1 mg per kg of body weight. A preferred dose for mucosal delivery (e.g. pulmonary delivery such as nasal delivery) is from about 0.01 μg to 10 mg per kilogram body weight, such as from 0.1 μg to 1 mg. Preferably the dose is less than 0.5, 0.2 or 0.1 mg per kg of body weight. Where multiple doses are required the doses referred to above are typically per day.

The amount of inhibitory nucleic acid or active ingredient that can be combined with suitable carrier materials to produce a single dosage form varies depending upon the host treated and the particular mode of administration. It is understood that the specific dose level for any particular subject depends upon a variety of factors including the activity of the specific compound employed, the age, body weight, general health, sex, diet, time of administration, route of administration, and rate of excretion, drug combination and the severity of the particular disease undergoing therapy.

The nucleic acid molecules of the present invention can also be administered to a subject in combination with other therapeutic compounds or treatments, such as radiation, to increase the overall therapeutic effect.

An "effective amount" is an amount of a therapeutic agent sufficient to achieve the intended purpose. The effective amount of a given therapeutic agent will vary with factors such as the nature of the agent, the route of administration, the size and species of the animal to receive the therapeutic agent, and the purpose of the administration. The effective amount in each individual case may be determined empirically by a skilled artisan according to established methods in the art.

The present invention will now be further described with reference to the following example, which are illustrative only and non-limiting. The examples refer to figures:

DESCRIPTION OF THE FIGURES

FIG. 2 is a graph showing the size of secondary tumours obtained following injection of TC-1 tumour cells into normal mice previously injected with TC-1 tumour cells treated with different shRNA constructs.

FIG. 3 is a graph showing the size of secondary tumours obtained following injection of: A. TC-1 tumour cells into Rag-/- mice previously injected with TC-1 tumour cells treated with different shRNA constructs; and B. TC-1 tumour cells into normal mice previously injected with C2 tumour cells treated with different shRNA constructs.

FIG. 4A is a schematic representation of the target mRNA which encodes the full length OVA protein. The target sites for OVA1, OVA 2 and OVA 3 are shown. (771-792=SIINFEKL (SEQ ID NO: 21)=the dominant CTL epitope of Ovalbumin, 165-186=a sub-dominant CTL epitope, 528-552=another subdominant epitope; and 786-828 and 969-1017 are CD4 helper epitopes).

FIG. 4B shows the weights of challenge tumours arising from cells expressing the different OVA shRNA constructs as described above.

EXAMPLES

Figure 1:
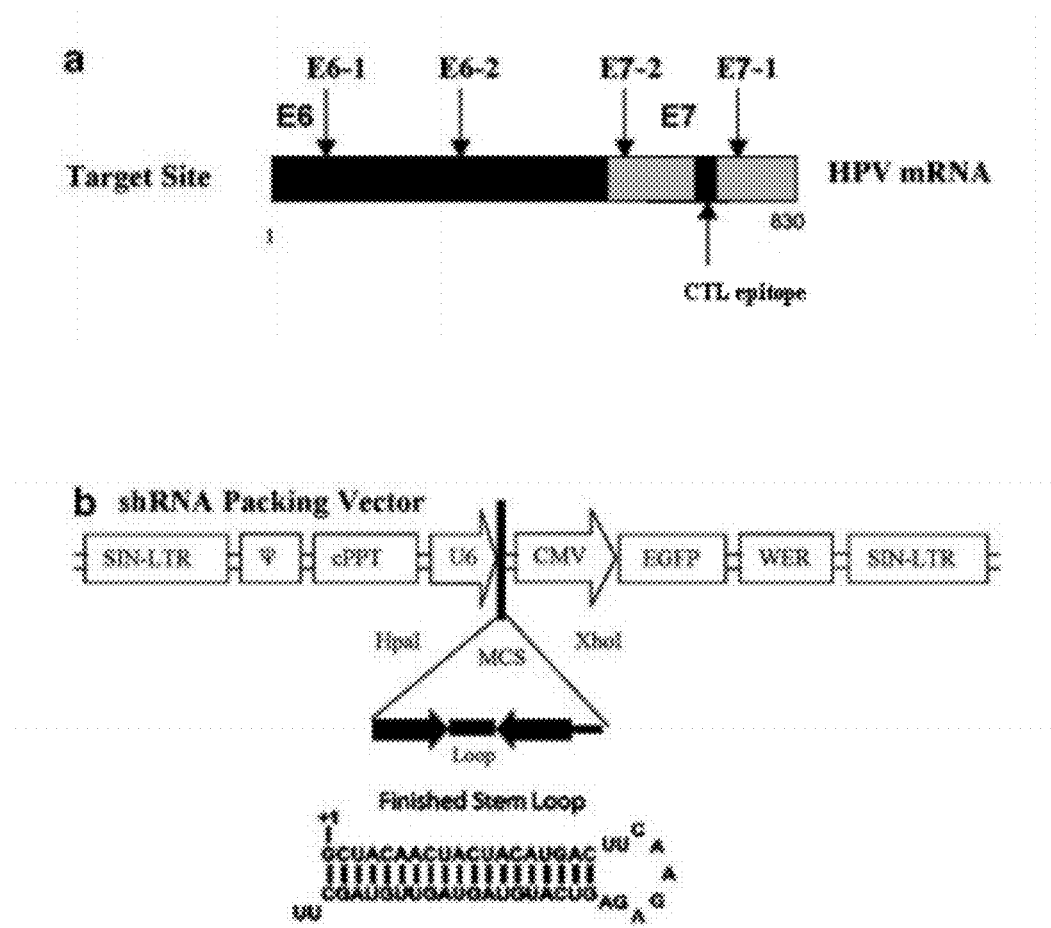
FIG. 1 is a schematic representation of a. the target mRNA which encodes the full length HPV E6/E7 proteins. The target sites for shRNA E6-1 (nts 417 to 434), E6-2 (nts 136-153), E7-1 (nts 181 to 198) and E7-2 (nts 4 to 21) are shown; and b. lentiviral packaging vector structure. The expression cassette is under the control of a U6 promoter (HpaI and XhoI site). The finished stem loop (SEQ ID NO: 22) shows a representative hairpin structure of the transcribed shRNA.

Materials and Methods shRNA Design and Lentiviral Packing Plasmids

We followed the criteria described by Tom Tuschl and used the computer program (web site http://www.mpibpc.g-wdg.de/abteilungen/100/105/sirna.html) to design shRNAs based on an HPV16 E6 mRNA sequence. Two of them were specially chosen for this study, shE6-1 targets at the common sites of all mRNA classes, whereas shE6-2 targets only class I mRNA. We also designed two more shRNAs, shE7-1 and shE7-2, based on the HPV16 E7 mRNA sequence. shE7-1 was designed to target a region downstream of the major E6/E7 cytotoxic T cell (CTL) epitope sequence and shE7-2 was designed to target a region upstream of the major E6/E7

CTL epitope sequence. The nucleotide and amino acid sequences of HPV16 E6 and E7 are shown in the sequence listing as SEQ ID NOs 1 and 2, respectively.

The shRNA expression cassette contained 18 nucleotides (nts) of the target sequence followed by the loop sequence (TTCAAGA GA), reverse complement to the 18 nts, stop codon for U6 promoter and Xho1 site. (first 18 nt located at: shE6-2 nts 136 to 153 and shE6-1 at nts 417 to 434 of SEQ ID NO:1; shE7-1 nts 181 to 198 and shE7-2 nts 4 to 21 of SEQ ID NO:2).

HPV 16 E6-1:

(SEQ ID NO: 5)
5'TGACCGGTCGATGTATGTCTTCAAGAGAGACATACATCGACGGTCT

TTTTTC 3'

(SEQ ID NO: 6)
3'ACTGGCCAGCTACATACAGAAGTTCTCTCTGTATGTAGCTGCCACA

AAAAAGAGCT 5'

HPV 16E6-2:

(SEQ ID NO: 7)
5'TCGACGTGAGGTATATGACTTCAAGAGAGTCATATACCTCACGTCG

TTTTTTC 3'

(SEQ ID NO: 8)
3'AGCTGCACTCCATATACTGAAGTTCTCTCAGTATATGGAGTGCAGC

AAAAAAGAGCT 5'

HPV 16E7-1:

(SEQ ID NO: 9)
5'TGTGTGACTCTACGCTTCGGTTCAAGAGACCGAAGCGTAGAGTCAC

ATTTTTTC 3'

(SEQ ID NO: 10)
3'ACACACTGAGATGCGAAGCCAAGTTCTCTGGCTTCGCATCTCAGTG

TAAAAAAGAGCT 5'

HPV 16E7-2:

(SEQ ID NO: 11)
5'TCATGGAGATACACCTACATTCAAGAGATGTAGGTGTATCTCCATG

TTTTTTC 3'

(SEQ ID NO: 12)
3'AGTACCTCTATGTGGATGTAAGTTCTCTACATCCACATAGAGGTAC

AAAAAGAGCT 5'

The shRNA cassettes and their complementary strands were synthesized (PROLIGO, Lismore, Australia) and annealed in the annealing buffer (100 mM K-acetate, 30 mM HEPES-KOH (pH 7.4), 2 mM Mg-acetate) by heating to 95° C. for 5 min followed by cooling to room temperature. The resulting double-strand oligo-DNA was cloned into plasmid pLentiLox3.7 (pLL3.7, a gift from Dr Luk van Parijs, MIT, Cambridge) at the HapI and XhoI sites (FIG. 1). The insert was confirmed by both restriction enzyme digestion and DNA sequencing. As FIG. 1 indicates, Plasmid pLLl3.7 (transfer vector) has a self-inactivating LTR for biosafety. Plasmid pLL3.7 also contains an eGFP gene under cytomegalovirus (CMV) promoter; this enables monitoring the infection of lentiviruses by eGFP expression. The lentiviral packaging plasmids pRSVRev, pMDLgpRRE and pMD.G (contains VSV.G gene) were a gift from Dr Inda Vermer (Salk Institute, San Diego, Calif.). These packaging plasmids are described in detail by Dull et al., 1998, J Virol. 72: 8463-8471 and were used for third-generation lentiviral vector production.

Production of Lentiviruses

Lentiviral production and titration were as previously described (Putral et al., 2005, Mol. Pharmacol 68: 1311-1319). Briefly, the packing plasmids and pLL3.7 were amplified in *E. coli* and purified using W/Endo-free Qiagen Maxi-Prep Kits (Promega, Sydney Australia) according to the manufacturer's instructions. Packing cell line 293T cells were transfected with 6.6 µg pLL3.7 (−/+ insert) and 3.3 µg of each packaging plasmid in 133 µl 1.25M $CaCl_2$, 0.5 ml $H_2O$, and 0.66 ml 2×HBS (140 mM NaCl, 1.5 mM $Na_2HPO_4$, 50 mM HEPES, pH 7.05) in a $T_{75}$ flask. The viral supernatant was harvested and concentrated 40-50 times using Vivaspin 20 ml Concentrators (100 MW, VivaScience Sartorius Group, Sydney Australia). The lentiviral stocks were stored in small aliquot at −80° C. for titration and cell infection.

Cell Infection

TC-1 cells were plated in 6-well plates ($1 \times 10^5$ cells/well) and were cultured overnight. Lentiviruses were diluted in 0.5 ml DMEM medium containing polybrene (8 µg/ml) and added to the cells for incubation for 1 hour at 37° C. After this, 1 ml of fresh polybrene-DMEM was added to the cells and incubation continued for 24 hours. After 24 hours infection, polybrene-DMEM was replaced with fresh DMEM medium and the cells were cultured for other assays.

Animal Procedures

TC-1 cells were infected with lentiviruses as described above and harvested 2 days post-infection. The cells were washed with PBS, counted, and resuspended in PBS at $1 \times 10^7$/ml. Female mice (5-6 weeks old, 5-10 mice/group) were injected with 0.1 ml cell suspension subcutaneously to the neck scruff. All experiments were approved by the University of Queensland Animal Ethics Committee.

Western Blotting

Cell lysates were prepared by trypsinizing the cells and resuspending them in RIPA buffer plus protein inhibitory cocktails (0.1%). For analysis of apoptosis, the cell lysates were prepared from an aliquot of cells cultured as described below for animal injection. For electrophoresis, 30-40 µg of total protein in 2× loading buffer was loaded to each well of a 10% (w/v) SDS-PAGE gel. After electrotransfer, the blot was blocked and probed with primary antibody at 4° C. followed by incubation with HRP-conjugated secondary antibody (1:2000 dilution) and then bound antibody was detected by ECL (Amersham). Anti-mouse β-tubulin antibody was from Sigma. Primary antibodies were used at a 1/1000 dilution.

Example 1

Induction of an Immune Response Against Viral Antigens by RNAi

TC-1 tumour cells were pre-treated with lentiviral vectors expressing one of the following shRNA molecules: shRNA 16E6-1; shRNA 16E6-2, shRNA 16E7-1 and shRNA 16E7-2 (see FIG. 1 for a schematic representation of the regions of E6/E7 against which the shRNAs are targeted). TC-1 cells are a tumourigenic, H-$2^b$ cell line expressing the E6 and E7 proteins of HPV16 (Lin, et al., 1996. Cancer Res. 56: 21-26). The cells were then injected into C57BL/6 mice (syngeneic with the tumour cells) and allowed to establish for 10 days. After this period of time parental tumour TC-1 cells that have not been treated in any way were injected into the mice. The mice were then analysed at day 17 to determine whether the secondary tumour cells could grow, i.e. to determine whether the mice have mounted an immune response against the E6 or E7 protein, which then inhibits growth of the injected secondary tumour cells.

The results shown in FIG. 2 show that the size of the secondary, challenge tumours differs depending on the shRNA used. E7-1 shRNA results in very small secondary tumours whereas the other shRNAs, targeted before the known CTL epitope, do not (data not shown for E6-2 shRNA).

The differences in results obtained for different shRNA constructs were not due to differing levels of knockdown since the levels of E7 protein were found to be reduced to the same degree in each case (data not shown).

The shRNAs delivered by lentiviral vectors all suppress E7 protein expression by about 50%. To investigate whether this reduction in E7 expression in TC-1 cells would affect the antigen presentation to cytotoxic T cells of the E7 CTL epitope, a CTL assay was performed. Our results indicate that the reduction in E7 expression in TC-1 cells did not affect their ability to be lysed by specific cytotoxic T cells (data not shown).

To further confirm this, another tumour cell line, C2, was employed. C2 cells are tumour cells that express HPV E7, but do not require E7 for viability. The results demonstrated that C2 cells transduced with shE7-1 also had reduced E7 expression (data not shown) but that, again, the reduction in E7 expression did not affect cell lysis by specific cytotoxic T cells as compared with non-transduced C2 cells which expressed normal levels of E7 protein (data not shown). Therefore, the results from both TC-1 cells and C2 cells showed that although E7 expression was reduced, cell lysis by specific cytotoxic T cells was not affected.

It was also investigated whether a functional immune system was required to obtain the observed results detailed above. The same experiment outlined above was carried out in mice with no adaptive immune system (i.e. Rag-/- mice). It was observed that normal tumour growth was restored in mice without an adaptive immune system, as opposed to the mice with an immune system in which inhibition of secondary tumour growth was observed. (FIG. 3A—data not shown for E7-2 shRNA). This result demonstrates that the effect seen requires a functional immune system.

Further experiments were carried out to determine whether the reduction in secondary tumour growth was the result of cell death. Similar experiments as described above were carried out using C2 cells infected with lentiviruses expressing either E7-1 or E7-2 shRNA. C2 cells are tumour cells that express HPV E7, but do not require E7 for viability. It was found that the shRNA E7-1 construct retained the ability to inhibit secondary tumour growth in these cells (FIG. 3B). This demonstrates that the results seen are not due to cell death of the primary tumour cells, i.e. that the immune response is not the result of cell apoptosis.

Discussion

Our results show that of the four different shRNA constructs used to target E6 and E7 sequences, E7-1 shRNA, led to a significant reduction in secondary tumour growth as compared with the other three constructs as well as the controls. E7-1 shRNA targets a site within the E6/E7 mRNA downstream of a region encoding a major CTL epitope, whereas the other shRNAs are all targeted to sites upstream of that region. This leads us to conclude that the effect seen with the E7-1 shRNA is due to "enhanced immune presentation" of the major E7 CTL epitope.

The shRNA cuts the mRNA and conventional wisdom would say that the mRNA is then degraded quickly. In our view, however, some mRNA is translated but as a result of the shRNA binding to the mRNA, the resulting protein is recognised by the cell as defective or aberrant (e.g. a truncated protein is produced which is misfolded etc.) and sent to the proteosome as rubbish. The proteosome processes proteins for presentation via MHC class I as part of normal cell processes but only certain parts of the protein will be presented and elicit an immune response—CTL epitopes for example. Targeting of the shRNA downstream of the CTL epitope may allow for greater translation of that region of the polypeptide compared with the shRNAs that are targeted further upstream. As a result, there is now more immune presentation of the E7 CTL epitope and a greater immune response.

Accordingly, RNAi moieties can be designed to target a region downstream of known or predicted T cell epitopes so as to produce an incomplete mRNA. Multiple T cell epitopes could be targeted with a single protein by using multiple RNAi's.

Example 2

Induction of an Immune Response Against OVA by RNAi

To further investigate the results obtained above, we selected three shRNAs (OVA1, OVA 2 and OVA3) to target the OVA mRNA sequence (See FIG. 4A).

OVA 1 and OVA2, as depicted in FIG. 4A, were designed to target a region of the OVA mRNA sequence that is downstream of a sub-dominant CTL epitope located at nucleotides +165 to +186. OVA 3 was designed to target a region of the OVA mRNA sequence that is downstream of the dominant CTL epitope located at nucleotides +771 to +792. Other T cell epitopes present in the OVA is sequence are shown in FIG. 4A.

The shRNA expression cassettes contained 19 nt of the target sequence, followed by the loop sequence (TTCAA-GAGA), reverse complement to the 19 nt, a stop codon for U6 promoter, and an Xho1 site. The sequences of the shRNAs were as follows.

```
OVA1:
                                          (SEQ ID NO: 15)
5'-TACCAAATGATGTTTATTCGTTTCAAGAGAACGAATAAACATCAT

TTGGTATTTTTC

OVA2:
                                          (SEQ ID NO: 17)
5' TGGAACTGTATAGAGGAGGCTTTCAAGAGAAGCCTCCTCTATACA

GTTCCATTTTTC

OVA3:
                                          (SEQ ID NO: 19)
5' TATACAACCTCACATCTGTCTTTCAAGAGAAGACAGATGTGAGGT

TGTATATTTTTC
```

The shRNA cassettes and their complementary strands were synthesised as described above.

Manipulation of cells, cell transductions and animal infection procedures were carried out essentially as described above except that LV-shRNAs targeting OVA were used with EG7 cells as the primary tumor while the challenge tumor was untreated EG7 cells. The EG7 cell line, like C2, is derived from EL4 thymoma cells but expresses the ovalbumin (OVA) antigen.

Results

Using a second tumor model system, based upon the EG7 cell line, which, like C2, is derived from EL4 thymoma cells but which expresses the ovalbumin (OVA) antigen, we cloned the three OVA-specific shRNAs into our lentiviral system and transduced EG7 cells. We found that all three OVA-specific shRNAs were able to specifically reduce the abundance of OVA protein in these cells. However, Western blotting for OVA protein indicated that levels of expression were substantially lower in cells targeted with the OVA3 shRNA construct as compared with cells treated with the OVA1 or OVA2 shRNA constructs (data not shown). Furthermore, Western blotting indicated the presence of truncated OVA polypeptides in OVA1 and OVA2 treated cells (which, as would be predicted, were larger in OVA2-treated cells than in OVA1-treated cells—data not shown).

The immunization-challenge experiments were repeated as before by injecting shRNA-transduced EG7 cells into mice and then 10 days later injecting non-transduced EG7 cells. Mice immunized with OVA2-transduced cells were protected against tumour development following immunization challenge. Less protection was noted in OVA1 immunized mice while immunization with vector control or OVA3-transduced cells afforded no protection (FIG. 4B).

Discussion we tested our immunization-challenge system using a second tumor model system based on OVA, We found that 2 of the three OVA-specific shRNAs were able to enhance immunity against OVA. Interestingly, an shRNA construct which targets a sequence downstream of a region encoding a dominant CTL epitope did not lead to enhanced immunity whereas constructs which targeted downstream of subdominant epitopes but upstream of this CTL epitope did lead to enhanced immunity. However, Western blots of cell extracts indicate that in the case of OVA3, little to no OVA protein is actually being produced in the cells i.e. strong silencing of OVA expression is occurring such that there is little or no protein that is available to be processed and presented to the immune system. By contrast, the OVA1 and OVA2 results indicate the presence of significant levels of truncated protein. These data are therefore consistent with the hypothesis presented above that expression of aberrant protein which can be processed and presented, is responsible for the enhancement of the immune response. Further, these data indicate that RNAi can enhance immunity not only against a viral antigen, E7, but also against exogenous antigens such as OVA. Furthermore, the results with OVA, which has a number of T cell epitopes, indicate that multiple T cell epitopes could be targeted within a single protein by using multiple RNAi's designed for strategic locations on the target polypeptide.

The various features and embodiments of the present invention, referred to in individual sections above apply, as appropriate, to other sections, mutatis mutandis. Consequently features specified in one section may be combined with features specified in other sections, as appropriate.

All publications mentioned in the above specification are herein incorporated by reference. Various modifications and variations of the described methods and products of the invention will be apparent to those skilled in the art without departing from the scope of the invention. Although the invention has been described in connection with specific preferred embodiments, it should be understood that the invention as claimed should not be unduly limited to such specific embodiments. Indeed, various modifications of the described modes for carrying out the invention which are apparent to those skilled in the relevant fields are intended to be within the scope of the following claims.

We claim:

1. A method of inducing or enhancing an immune response in a mammal to an E6/E7 polypeptide of HPV, comprising administering to the mammal an shRNA which targets an E6/E7 region of an HPV RNA consisting of nucleotides 181-198 of SEQ ID NO: 3, at least a portion of the E6/E7 polypeptide comprising a T cell epitope and presented on a surface of cells bound to major histocompatibility complex (MHC), the shRNA comprising an antisense strand consisting of a sequence complementary to nucleotides 181-198 of SEQ ID NO: 3, and wherein the administered shRNA is insufficient to kill directly cells expressing the E6/E7 polypeptide.

2. The method of claim 1, wherein the shRNA is administered at a dosage of 0.01 μg to 1 mg per kilogram body weight of the mammal.

3. The method of claim 1, wherein the mammal is a human.

4. The method of claim 1, wherein the shRNA is coupled to a liposome or a polymeric nanoparticle.

5. The method of claim 1, wherein the shRNA is covalently attached to polyethylene glycol.

6. The method of claim 1, wherein the shRNA is administered by injection.

7. The method of claim 1, wherein a duplex structure of the shRNA is 15-25 nucleotides in length.

8. The method of claim 1, wherein a duplex structure of the shRNA is 18 nucleotides in length.

9. The method of claim 1, wherein a single-stranded loop of the shRNA is 5-11 nucleotides in length.

10. The method of claim 1, wherein a single-stranded loop of the shRNA comprises the sequence TTCAAGAGA.

11. The method of claim 1, wherein the shRNA comprises a sense sequence comprising nucleotides 3-20 of SEQ ID NO: 9.

12. The method of claim 1, wherein the shRNA comprises a sense sequence consisting of nucleotides 3-20 of SEQ ID NO: 9.

13. The method of claim 11, wherein the shRNA comprises SEQ ID NO: 9.

14. The method of claim 11, wherein the shRNA consists of SEQ ID NO: 9.

\* \* \* \* \*

SEQUENCE LISTING

```
<160> NUMBER OF SEQ ID NOS: 22

<210> SEQ ID NO 1
<211> LENGTH: 477
<212> TYPE: DNA
<213> ORGANISM: Human papillomavirus
<220> FEATURE:
<221> NAME/KEY: CDS
<222> LOCATION: (1)..(474)

<400> SEQUENCE: 1 atg cac caa aag aga act gca atg ttt cag gac cca cag gag cga ccc      48
Met His Gln Lys Arg Thr Ala Met Phe Gln Asp Pro Gln Glu Arg Pro
1               5                   10                  15 aga aag tta cca cag tta tgc aca gag ctg caa aca act ata cat gat      96
Arg Lys Leu Pro Gln Leu Cys Thr Glu Leu Gln Thr Thr Ile His Asp
            20                  25                  30 ata ata tta gaa tgt gtg tac tgc aag caa cag tta ctg cga cgt gag     144
Ile Ile Leu Glu Cys Val Tyr Cys Lys Gln Gln Leu Leu Arg Arg Glu
        35                  40                  45 gta tat gac ttt gct ttt cgg gat tta tgc ata gta tat aga gat ggg     192
Val Tyr Asp Phe Ala Phe Arg Asp Leu Cys Ile Val Tyr Arg Asp Gly
    50                  55                  60 aat cca tat gct gta tgt gat aaa tgt tta aag ttt tat tct aaa att     240
Asn Pro Tyr Ala Val Cys Asp Lys Cys Leu Lys Phe Tyr Ser Lys Ile
65                  70                  75                  80 agt gag tat aga cat tat tgt tat agt ttg tat gga aca aca tta gaa     288
Ser Glu Tyr Arg His Tyr Cys Tyr Ser Leu Tyr Gly Thr Thr Leu Glu
                85                  90                  95 cag caa tac aac aaa ccg ttg tgt gat ttg tta att agg tgt att aac     336
Gln Gln Tyr Asn Lys Pro Leu Cys Asp Leu Leu Ile Arg Cys Ile Asn
```

```
tgt caa aag cca ctg tgt cct gaa gaa aag caa aga cat ctg gac aaa        384
Cys Gln Lys Pro Leu Cys Pro Glu Glu Lys Gln Arg His Leu Asp Lys
            115                 120                 125 aag caa aga ttc cat aat ata agg ggt cgg tgg acc ggt cga tgt atg        432
Lys Gln Arg Phe His Asn Ile Arg Gly Arg Trp Thr Gly Arg Cys Met
130                 135                 140 tct tgt tgc aga tca tca aga aca cgt aga gaa acc cag ctg taa            477
Ser Cys Cys Arg Ser Ser Arg Thr Arg Arg Glu Thr Gln Leu
145                 150                 155

<210> SEQ ID NO 2
<211> LENGTH: 158
<212> TYPE: PRT
<213> ORGANISM: Human papillomavirus

<400> SEQUENCE: 2

Met His Gln Lys Arg Thr Ala Met Phe Gln Asp Pro Gln Glu Arg Pro
1               5                   10                  15

Arg Lys Leu Pro Gln Leu Cys Thr Glu Leu Gln Thr Thr Ile His Asp
                20                  25                  30

Ile Ile Leu Glu Cys Val Tyr Cys Lys Gln Gln Leu Leu Arg Arg Glu
            35                  40                  45

Val Tyr Asp Phe Ala Phe Arg Asp Leu Cys Ile Val Tyr Arg Asp Gly
        50                  55                  60

Asn Pro Tyr Ala Val Cys Asp Lys Cys Leu Lys Phe Tyr Ser Lys Ile
65                  70                  75                  80

Ser Glu Tyr Arg His Tyr Cys Tyr Ser Leu Tyr Gly Thr Thr Leu Glu
                85                  90                  95

Gln Gln Tyr Asn Lys Pro Leu Cys Asp Leu Leu Ile Arg Cys Ile Asn
                100                 105                 110

Cys Gln Lys Pro Leu Cys Pro Glu Glu Lys Gln Arg His Leu Asp Lys
            115                 120                 125

Lys Gln Arg Phe His Asn Ile Arg Gly Arg Trp Thr Gly Arg Cys Met
130                 135                 140

Ser Cys Cys Arg Ser Ser Arg Thr Arg Arg Glu Thr Gln Leu
145                 150                 155

<210> SEQ ID NO 3
<211> LENGTH: 297
<212> TYPE: DNA
<213> ORGANISM: Human papillomavirus
<220> FEATURE:
<221> NAME/KEY: CDS
<222> LOCATION: (1)..(294)

<400> SEQUENCE: 3 atg cat gga gat aca cct aca ttg cat gaa tat atg tta gat ttg caa        48
Met His Gly Asp Thr Pro Thr Leu His Glu Tyr Met Leu Asp Leu Gln
1               5                   10                  15 cca gag aca act gat ctc tac tgt tat gag caa tta aat gac agc tca        96
Pro Glu Thr Thr Asp Leu Tyr Cys Tyr Glu Gln Leu Asn Asp Ser Ser
                20                  25                  30 gag gag gag gat gaa ata gat ggt cca gct gga caa gca gaa ccg gac       144
Glu Glu Glu Asp Glu Ile Asp Gly Pro Ala Gly Gln Ala Glu Pro Asp
            35                  40                  45 aga gcc cat tac aat att gta acc ttt tgt tgc aag tgt gac tct acg       192
Arg Ala His Tyr Asn Ile Val Thr Phe Cys Cys Lys Cys Asp Ser Thr
        50                  55                  60
```

```
ctt cgg ttg tgc gta caa agc aca cac gta gac att cgt act ttg gaa    240
Leu Arg Leu Cys Val Gln Ser Thr His Val Asp Ile Arg Thr Leu Glu
 65                  70                  75                  80 gac ctg tta atg ggc aca cta gga att gtg tgc ccc atc tgt tct cag    288
Asp Leu Leu Met Gly Thr Leu Gly Ile Val Cys Pro Ile Cys Ser Gln
                 85                  90                  95 aaa cca taa                                                         297
Lys Pro
```

<210> SEQ ID NO 4
<211> LENGTH: 98
<212> TYPE: PRT
<213> ORGANISM: Human papillomavirus

<400> SEQUENCE: 4

```
Met His Gly Asp Thr Pro Thr Leu His Glu Tyr Met Leu Asp Leu Gln
  1               5                  10                  15

Pro Glu Thr Thr Asp Leu Tyr Cys Tyr Glu Gln Leu Asn Asp Ser Ser
                 20                  25                  30

Glu Glu Glu Asp Glu Ile Asp Gly Pro Ala Gly Gln Ala Glu Pro Asp
             35                  40                  45

Arg Ala His Tyr Asn Ile Val Thr Phe Cys Cys Lys Cys Asp Ser Thr
 50                  55                  60

Leu Arg Leu Cys Val Gln Ser Thr His Val Asp Ile Arg Thr Leu Glu
 65                  70                  75                  80

Asp Leu Leu Met Gly Thr Leu Gly Ile Val Cys Pro Ile Cys Ser Gln
                 85                  90                  95

Lys Pro
```

<210> SEQ ID NO 5
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
tgaccggtcg atgtatgtct tcaagagaga catacatcga cggtcttttt tc            52

<210> SEQ ID NO 6
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
tcgagaaaaa acaccgtcga tgtatgtctc tcttgaagac atacatcgac cggtca        56

<210> SEQ ID NO 7
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
tcgacgtgag gtatatgact tcaagagagt catatacctc acgtcgtttt ttc           53

```
<210> SEQ ID NO 8
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
tcgagaaaaa acgacgtgag gtatatgact ctcttgaagt catatacctc acgtcga        57

<210> SEQ ID NO 9
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
tgtgtgactc tacgcttcgg ttcaagagac cgaagcgtag agtcacattt tttc           54

<210> SEQ ID NO 10
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
tcgagaaaaa atgtgactct acgcttcggt ctcttgaacc gaagcgtaga gtcacaca       58

<210> SEQ ID NO 11
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
tcatggagat acacctacat tcaagagatg taggtgtatc tccatgtttt ttc            53

<210> SEQ ID NO 12
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
tcgagaaaaa acatggagat acacctacat ctcttgaatg taggtgtatc tccatga        57

<210> SEQ ID NO 13
<211> LENGTH: 1873
<212> TYPE: DNA
<213> ORGANISM: Gallus gallus
<220> FEATURE:
<221> NAME/KEY: CDS
<222> LOCATION: (66)..(1223)

<400> SEQUENCE: 13
gacatacagc tagaaagctg tattgccttt agcactcaag ctcaaaagac aactcagagt     60 tcacc atg ggc tcc atc ggc gca gca agc atg gaa ttt tgt ttt gat gta   110
      Met Gly Ser Ile Gly Ala Ala Ser Met Glu Phe Cys Phe Asp Val
```

-continued

|  | 1 |  |  |  | 5 |  |  |  | 10 |  |  |  |  | 15 |  |  |
|---|---|---|---|---|---|---|---|---|---|---|---|---|---|---|---|---|
| ttc | aag | gag | ctc | aaa | gtc | cac | cat | gcc | aat | gag | aac | atc | ttc | tac | tgc | 158 |
| Phe | Lys | Glu | Leu | Lys | Val | His | His | Ala | Asn | Glu | Asn | Ile | Phe | Tyr | Cys |  |
|  |  |  | 20 |  |  |  |  | 25 |  |  |  |  |  | 30 |  |  |

| ccc | att | gcc | atc | atg | tca | gct | cta | gcc | atg | gta | tac | ctg | ggt | gca | aaa | 206 |
| Pro | Ile | Ala | Ile | Met | Ser | Ala | Leu | Ala | Met | Val | Tyr | Leu | Gly | Ala | Lys |  |
|  |  |  | 35 |  |  |  |  | 40 |  |  |  |  | 45 |  |  |  |

| gac | agc | acc | agg | aca | cag | ata | aat | aag | gtt | gtt | cgc | ttt | gat | aaa | ctt | 254 |
| Asp | Ser | Thr | Arg | Thr | Gln | Ile | Asn | Lys | Val | Val | Arg | Phe | Asp | Lys | Leu |  |
|  |  | 50 |  |  |  |  | 55 |  |  |  |  | 60 |  |  |  |  |

| cca | gga | ttc | gga | gac | agt | att | gaa | gct | cag | tgt | ggc | aca | tct | gta | aac | 302 |
| Pro | Gly | Phe | Gly | Asp | Ser | Ile | Glu | Ala | Gln | Cys | Gly | Thr | Ser | Val | Asn |  |
| 65 |  |  |  |  | 70 |  |  |  |  | 75 |  |  |  |  |  |  |

| gtt | cac | tct | tca | ctt | aga | gac | atc | ctc | aac | caa | atc | acc | aaa | cca | aat | 350 |
| Val | His | Ser | Ser | Leu | Arg | Asp | Ile | Leu | Asn | Gln | Ile | Thr | Lys | Pro | Asn |  |
| 80 |  |  |  |  | 85 |  |  |  |  | 90 |  |  |  |  | 95 |  |

| gat | gtt | tat | tcg | ttc | agc | ctt | gcc | agt | aga | ctt | tat | gct | gaa | gag | aga | 398 |
| Asp | Val | Tyr | Ser | Phe | Ser | Leu | Ala | Ser | Arg | Leu | Tyr | Ala | Glu | Glu | Arg |  |
|  |  |  |  | 100 |  |  |  |  | 105 |  |  |  |  | 110 |  |  |

| tac | cca | atc | ctg | cca | gaa | tac | ttg | cag | tgt | gtg | aag | gaa | ctg | tat | aga | 446 |
| Tyr | Pro | Ile | Leu | Pro | Glu | Tyr | Leu | Gln | Cys | Val | Lys | Glu | Leu | Tyr | Arg |  |
|  |  |  | 115 |  |  |  |  | 120 |  |  |  |  | 125 |  |  |  |

| gga | ggc | ttg | gaa | cct | atc | aac | ttt | caa | aca | gct | gca | gat | caa | gcc | aga | 494 |
| Gly | Gly | Leu | Glu | Pro | Ile | Asn | Phe | Gln | Thr | Ala | Ala | Asp | Gln | Ala | Arg |  |
|  |  | 130 |  |  |  |  | 135 |  |  |  |  | 140 |  |  |  |  |

| gag | ctc | atc | aat | tcc | tgg | gta | gaa | agt | cag | aca | aat | gga | att | atc | aga | 542 |
| Glu | Leu | Ile | Asn | Ser | Trp | Val | Glu | Ser | Gln | Thr | Asn | Gly | Ile | Ile | Arg |  |
|  | 145 |  |  |  |  | 150 |  |  |  |  | 155 |  |  |  |  |  |

| aat | gtc | ctt | cag | cca | agc | tcc | gtg | gat | tct | caa | act | gca | atg | gtt | ctg | 590 |
| Asn | Val | Leu | Gln | Pro | Ser | Ser | Val | Asp | Ser | Gln | Thr | Ala | Met | Val | Leu |  |
| 160 |  |  |  |  | 165 |  |  |  |  | 170 |  |  |  |  | 175 |  |

| gtt | aat | gcc | att | gtc | ttc | aaa | gga | ctg | tgg | gag | aaa | aca | ttt | aag | gat | 638 |
| Val | Asn | Ala | Ile | Val | Phe | Lys | Gly | Leu | Trp | Glu | Lys | Thr | Phe | Lys | Asp |  |
|  |  |  | 180 |  |  |  |  | 185 |  |  |  |  | 190 |  |  |  |

| gaa | gac | aca | caa | gca | atg | cct | ttc | aga | gtg | act | gag | caa | gaa | agc | aaa | 686 |
| Glu | Asp | Thr | Gln | Ala | Met | Pro | Phe | Arg | Val | Thr | Glu | Gln | Glu | Ser | Lys |  |
|  |  | 195 |  |  |  |  | 200 |  |  |  |  | 205 |  |  |  |  |

| cct | gtg | cag | atg | atg | tac | cag | att | ggt | tta | ttt | aga | gtg | gca | tca | atg | 734 |
| Pro | Val | Gln | Met | Met | Tyr | Gln | Ile | Gly | Leu | Phe | Arg | Val | Ala | Ser | Met |  |
|  | 210 |  |  |  |  | 215 |  |  |  |  | 220 |  |  |  |  |  |

| gct | tct | gag | aaa | atg | aag | atc | ctg | gag | ctt | cca | ttt | gcc | agt | ggg | aca | 782 |
| Ala | Ser | Glu | Lys | Met | Lys | Ile | Leu | Glu | Leu | Pro | Phe | Ala | Ser | Gly | Thr |  |
|  | 225 |  |  |  |  | 230 |  |  |  |  | 235 |  |  |  |  |  |

| atg | agc | atg | ttg | gtg | ctg | ttg | cct | gat | gaa | gtc | tca | ggc | ctt | gag | cag | 830 |
| Met | Ser | Met | Leu | Val | Leu | Leu | Pro | Asp | Glu | Val | Ser | Gly | Leu | Glu | Gln |  |
| 240 |  |  |  |  | 245 |  |  |  |  | 250 |  |  |  |  | 255 |  |

| ctt | gag | agt | ata | atc | aac | ttt | gaa | aaa | ctg | act | gaa | tgg | acc | agt | tct | 878 |
| Leu | Glu | Ser | Ile | Ile | Asn | Phe | Glu | Lys | Leu | Thr | Glu | Trp | Thr | Ser | Ser |  |
|  |  |  |  | 260 |  |  |  |  | 265 |  |  |  |  | 270 |  |  |

| aat | gtt | atg | gaa | gag | agg | aag | atc | aaa | gtg | tac | tta | cct | cgc | atg | aag | 926 |
| Asn | Val | Met | Glu | Glu | Arg | Lys | Ile | Lys | Val | Tyr | Leu | Pro | Arg | Met | Lys |  |
|  |  |  | 275 |  |  |  |  | 280 |  |  |  |  | 285 |  |  |  |

| atg | gag | gaa | aaa | tac | aac | ctc | aca | tct | gtc | tta | atg | gct | atg | ggc | att | 974 |
| Met | Glu | Glu | Lys | Tyr | Asn | Leu | Thr | Ser | Val | Leu | Met | Ala | Met | Gly | Ile |  |
|  |  | 290 |  |  |  |  | 295 |  |  |  |  | 300 |  |  |  |  |

| act | gac | gtg | ttt | agc | tct | tca | gcc | aat | ctg | tct | ggc | atc | tcc | tca | gca | 1022 |
| Thr | Asp | Val | Phe | Ser | Ser | Ser | Ala | Asn | Leu | Ser | Gly | Ile | Ser | Ser | Ala |  |
|  | 305 |  |  |  |  | 310 |  |  |  |  | 315 |  |  |  |  |  |

| gag | agc | ctg | aag | ata | tct | caa | gct | gtc | cat | gca | gca | cat | gca | gaa | atc | 1070 |

```
Glu Ser Leu Lys Ile Ser Gln Ala Val His Ala His Ala Glu Ile
320                 325                 330                 335 aat gaa gca ggc aga gag gtg gta ggg tca gcg gag gct gga gtg gat         1118
Asn Glu Ala Gly Arg Glu Val Val Gly Ser Ala Glu Ala Gly Val Asp
                340                 345                 350 gct gca agc gtc tct gaa gaa ttt agg gct gac cat cca ttc ctc ttc         1166
Ala Ala Ser Val Ser Glu Glu Phe Arg Ala Asp His Pro Phe Leu Phe
                355                 360                 365 tgt atc aag cac atc gca acc aac gcc gtt ctc ttc ttt ggc aga tgt         1214
Cys Ile Lys His Ile Ala Thr Asn Ala Val Leu Phe Phe Gly Arg Cys
                370                 375                 380 gtt tcc cct taaaagaag aaagctgaaa aactctgtcc cttccaacaa                  1263
Val Ser Pro
        385 gacccagagc actgtagtat caggggtaaa atgaaaagta tgttctctgc tgcatccaga       1323
cttcataaaa gctggagctt aatctagaaa aaaaatcaga agaaattac actgtgagaa        1383
caggtgcaat tcacttttcc tttacacaga gtaatactgg taactcatgg atgaaggctt       1443
aagggaatga aattggactc acagtactga gtcatcacac tgaaaaatgc aacctgatac       1503
atcagcagaa ggtttatggg ggaaaaatgc agccttccaa ttaagccaga tatctgtatg       1563
accaagctgc tccagaatta gtcactcaaa atctctcaga ttaaattatc aactgtcacc       1623
aaccattcct atgctgacaa ggcaattgct tgttctctgt gttcctgata ctacaaggct       1683
cttcctgact tcctaaagat gcattataaa atcttataa ttcacatttc tccctaaact        1743
ttgactcaat catggtatgt tggcaaatat ggtatattac tattcaaatt gttttccttg       1803
tacccatatg taatgggtct tgtgaatgtg ctcttttgtt cctttaatca taataaaaac       1863
atgtttaagc                                                              1873
```

<210> SEQ ID NO 14
<211> LENGTH: 386
<212> TYPE: PRT
<213> ORGANISM: Gallus gallus

<400> SEQUENCE: 14

```
Met Gly Ser Ile Gly Ala Ala Ser Met Glu Phe Cys Phe Asp Val Phe
1               5                   10                  15

Lys Glu Leu Lys Val His His Ala Asn Glu Asn Ile Phe Tyr Cys Pro
                20                  25                  30

Ile Ala Ile Met Ser Ala Leu Ala Met Val Tyr Leu Gly Ala Lys Asp
                35                  40                  45

Ser Thr Arg Thr Gln Ile Asn Lys Val Val Arg Phe Asp Lys Leu Pro
    50                  55                  60

Gly Phe Gly Asp Ser Ile Glu Ala Gln Cys Gly Thr Ser Val Asn Val
65                  70                  75                  80

His Ser Ser Leu Arg Asp Ile Leu Asn Gln Ile Thr Lys Pro Asn Asp
                85                  90                  95

Val Tyr Ser Phe Ser Leu Ala Ser Arg Leu Tyr Ala Glu Glu Arg Tyr
                100                 105                 110

Pro Ile Leu Pro Glu Tyr Leu Gln Cys Val Lys Glu Leu Tyr Arg Gly
                115                 120                 125

Gly Leu Glu Pro Ile Asn Phe Gln Thr Ala Ala Asp Gln Ala Arg Glu
    130                 135                 140

Leu Ile Asn Ser Trp Val Glu Ser Gln Thr Asn Gly Ile Ile Arg Asn
145                 150                 155                 160
```

```
Val Leu Gln Pro Ser Ser Val Asp Ser Gln Thr Ala Met Val Leu Val
                165                 170                 175

Asn Ala Ile Val Phe Lys Gly Leu Trp Glu Lys Thr Phe Lys Asp Glu
            180                 185                 190

Asp Thr Gln Ala Met Pro Phe Arg Val Thr Glu Gln Glu Ser Lys Pro
        195                 200                 205

Val Gln Met Met Tyr Gln Ile Gly Leu Phe Arg Val Ala Ser Met Ala
    210                 215                 220

Ser Glu Lys Met Lys Ile Leu Glu Leu Pro Phe Ala Ser Gly Thr Met
225                 230                 235                 240

Ser Met Leu Val Leu Leu Pro Asp Glu Val Ser Gly Leu Glu Gln Leu
                245                 250                 255

Glu Ser Ile Ile Asn Phe Glu Lys Leu Thr Glu Trp Thr Ser Ser Asn
            260                 265                 270

Val Met Glu Glu Arg Lys Ile Lys Val Tyr Leu Pro Arg Met Lys Met
        275                 280                 285

Glu Glu Lys Tyr Asn Leu Thr Ser Val Leu Met Ala Met Gly Ile Thr
    290                 295                 300

Asp Val Phe Ser Ser Ser Ala Asn Leu Ser Gly Ile Ser Ser Ala Glu
305                 310                 315                 320

Ser Leu Lys Ile Ser Gln Ala Val His Ala Ala His Ala Glu Ile Asn
                325                 330                 335

Glu Ala Gly Arg Glu Val Val Gly Ser Ala Glu Ala Gly Val Asp Ala
            340                 345                 350

Ala Ser Val Ser Glu Glu Phe Arg Ala Asp His Pro Phe Leu Phe Cys
        355                 360                 365

Ile Lys His Ile Ala Thr Asn Ala Val Leu Phe Phe Gly Arg Cys Val
    370                 375                 380

Ser Pro
385

<210> SEQ ID NO 15
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
taccaaatga tgtttattcg tttcaagaga acgaataaac atcatttggt attttttc      58

<210> SEQ ID NO 16
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gaaaaaatac caaatgatgt ttattcgttc tcttgaaacg aataaacatc atttggta      58

<210> SEQ ID NO 17
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 17
tggaactgta tagaggaggc tttcaagaga agcctcctct atacagttcc attttttc        58

<210> SEQ ID NO 18
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
gaaaaaatgg aactgtatag aggaggcttc tcttgaaagc ctcctctata cagttcca        58

<210> SEQ ID NO 19
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
tatacaacct cacatctgtc tttcaagaga agacagatgt gaggttgtat attttttc        58

<210> SEQ ID NO 20
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
gaaaaaatat acaacctcac atctgtcttc tcttgaaaga cagatgtgag gttgtata        58

<210> SEQ ID NO 21
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ser Ile Ile Asn Phe Glu Lys Leu
1               5

<210> SEQ ID NO 22
<211> LENGTH: 49
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
gcuacaacua cuacaugacu ucaagagagu caugucuag uuguagcuu                   49